United States Patent [19]

Pansegrau

[11] Patent Number: 6,013,841
[45] Date of Patent: Jan. 11, 2000

[54] METHOD FOR THE CONVERSION OF 3- AND 4-METHYLCATECHOL TO BENZALDEHYDE

[75] Inventor: Paul D. Pansegrau, Beulah, N. Dak.

[73] Assignee: Dakota Gasification Company, Beulah, N.C.

[21] Appl. No.: 09/126,482

[22] Filed: Jul. 30, 1998

Related U.S. Application Data

[63] Continuation-in-part of application No. 08/895,795, Jul. 17, 1997, abandoned.

[51] Int. Cl.[7] .................................................. C07C 45/43
[52] U.S. Cl. .......................... 568/437; 568/649; 568/651; 570/191
[58] Field of Search .................................... 568/437, 649, 568/651; 570/191

[56] References Cited

U.S. PATENT DOCUMENTS

| | | | |
|---|---|---|---|
| 4,145,494 | 3/1979 | Neubert | 526/81 |
| 4,335,263 | 6/1982 | Minai | 568/437 |
| 4,709,100 | 11/1987 | Hermolin et al. | 568/639 |

OTHER PUBLICATIONS

Hill et al, J.Chem.Soc. Perkin Trans. 1, pp. 2209–2215, 1987.

*Primary Examiner*—Shailendra Kumar
*Assistant Examiner*—Sreeni Padmanabhan
*Attorney, Agent, or Firm*—Alix, Yale & Ristas, LLP

[57] ABSTRACT

The 3- and 4-methylcatechols are converted to the corresponding benzaldehyde by first alkylating the hydroxyl groups to form an alkylated methylcatechol. The methyl group is then converted to a methyl dibromide group using 1,3-dibromo-5,5-dimethylhydantoin in the presence of a non-polar, non-reactive solvent such as carbon tetrachloride and heptane and a radical initiator having a ten hour half-life temperature in the range of 47° to 55° C. The dibromide is then hydrolyzed to form the aldehyde.

4 Claims, No Drawings

METHOD FOR THE CONVERSION OF 3- AND 4-METHYLCATECHOL TO BENZALDEHYDE

RELATED APPLICATION

This application is a continuation-in-part of pending U.S. application Ser. No. 08/895,795 filed Jul. 17, 1997 entitled "Method for the Conversion of 3- and 4-Methylcatechol to Benzaldehyde" which is incorporated herein by reference.

FIELD OF THE INVENTION

A method is described wherein either 3-methylcatechol or 4-methylcatechol is subjected to a series of chemical reactions in which the hydroxyl groups are converted to alkoxy-groups or a methylenedioxy bridge, and the benzylic methyl groups of the catechol are oxidized to the aldehyde. Such benzaldehydes are useful materials of commerce by themselves, or for conversion to other materials such as pyrogallol or homoveratrylamine.

BACKGROUND OF THE INVENTION

The conversion of aromatic methyl groups to the benzaldehydes (the simplest example being the oxidation of toluene) may be achieved by a number of methods. All methods are included in a group of reactions termed oxidations. Such oxidations may be accomplished by a number of reagent chemicals. Factors which differentiate the reagent chemicals from the standpoint of fitness for a particular application include cost, selectivity, efficiency, waste materials produced and the desired scale of reaction.

Typical reagent chemicals employed for the oxidation of aromatic methyl groups include metals at a high oxidation level such as cobalt, manganese, chromium, cerium, iron or copper. Non-metallic reagents include persulfate and peroxides, but these may frequently require a metallic catalyst. Air or oxygen may also be used as an oxidant, but the use of a metallic catalyst is almost always required.

A number of industrial processes have been described for the oxidation of aromatic methyl groups, with most employing a metal catalyst and an inexpensive oxidant such as air, oxygen, or ozone. Some of these processes employ a solvent under batch type conditions, while others are run without a solvent in a continuous type reactor.

The oxidation of the methylcatechols is a special instance in the family of reactions briefly described above. The use of a metal catalyst and either air or oxygen under appropriate conditions does result in formation of the desired benzaldehyde. However, significant byproduct information is also encountered under the test conditions employed. To date, for the methylcatechols, no metal catalyzed air or oxygen oxidation has resulted in an industrially viable process. This is borne out by prior descriptions of oxidations of methylcatechols and their analogs. U.S. Pat. No. 4,335,263 describes a process wherein the oxidation of methylcatechol analogs to benzaldehydes is achieved through the use of molecular bromine under radical conditions followed by further oxidation with dimethylsulfoxide. Another prior process utilizes molecular chlorine, again under radical conditions, to obtain the corresponding benzoic acids (after hydrolysis of the trichloride intermediate) rather than the benzaldehydes.

SUMMARY OF THE INVENTION

The present invention relates to a method for the conversion of 3- and 4-methylcatechols to the corresponding benzaldehyde and utilizes chemical reagents which contain bromine, and are known to oxidize aromatic methyl groups under radical conditions. The specific reagent is 1,3-dibromo-5,5-dimethylhydantoin (DBDMH). Under the conditions of the present invention, which include use of a non-polar, non-reactive solvent at elevated temperature and the use of a radical initiator, the bromine is smoothly transferred from the organic reagent chemical to the methyl group of the catechol analog. Simultaneously, the hydrogen of the methyl group is transferred to the reagent chemical. The net result is a trade of bromine and hydrogen between the organic reagent chemical and the methylcatechol analog to produce the dibromide.

DESCRIPTION OF THE PREFERRED EMBODIMENTS

In accordance with the present invention, a method is provided for the conversion of 3- or 4-methylcatechol to a desired benzaldehyde. The reaction scheme of the invention using 3-methylcatechol as the example is as follows:

Reaction Scheme

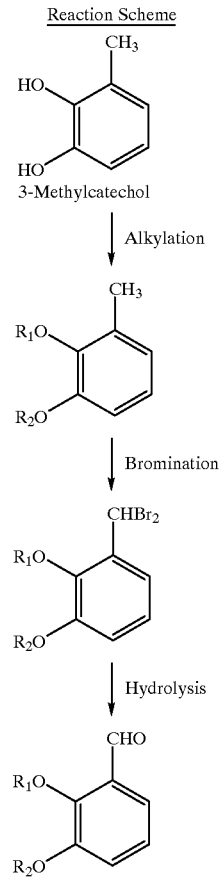

Where: $R_1$ and $R_2$ = Alkyl Groups

Referring to the above reaction scheme, the first step in the reaction of the methylcatechols is an oxygen alkylation reaction in which the hydroxyl groups are alkylated to protect these groups from reacting during the remainder of the process. The alkyl groups $R_1$ and $R_2$ will normally be the same where $R_1=R_2$ but that need not be the case. Also, these groups are generally from $C_1$ to $C_6$ alkyl groups although longer chain alkyl groups may also be utilized. Such oxygen alkylation reactions are known to those skilled in the art and involve treatment with reagents and under conditions such as those detailed in the examples hereinafter. The amount of oxygen alkylating reagent used may vary between 1 and 6 molar equivalents, preferably 1.5 to 3. The amount of solvent used may vary between amounts which provide a solution of 0.10 to 10 molar concentration, preferably 0.5 to 3.0 molar. Depending upon the exact type of oxygen alkylation reaction being performed, additional reagents may be appropriate such as acids, bases or catalysts as known in the art. The alkylated methylcatechols which are produced are most normally purified prior to subsequent use.

The next step in the process of the present invention is to subject the alkylated methylcatechols to an oxidation reaction using a brominating agent in a non-reactive, non-polar solvent for the production of the reactive dibromide. The brominating agent oxidizes the aromatic methyl groups under reaction conditions which nurture a reaction that proceeds via a chain-radical mechanism. Such conditions exclude air, especially oxygen, moisture and other environmental contaminants which would inhibit the propagation of the radical chain mechanism. Radical chain mechanisms are self-propagating, but must be initiated by a separate chemical entity as discussed later. The brominating agent of the present invention is 1,3-dibromo-5,5-dimethylhydantoin (DBDMH). The DBDMH brominating agent of the present invention has distinct advantages over molecular bromine as a brominating agent and advantages even over other brominating agents having the bromine attached to an organic molecule such as N-bromosuccinimide (NBS). With respect to the use of molecular bromine such as disclosed in U.S. Pat. No. 4,335,263, a lengthy reaction time is required since the molecular bromine must be added slowly because of the high reactivity of the bromine. Using the DBDMH of the present invention, the organic carrier molecule attenuates the reactivity which permits a more rapid addition and a much shorter time. The result is an increase in the rate of the desired reaction while decreasing the rate of undesired reactions. Using molecular bromine, the product is a mixture of mono-bromo (benzl bromide) and di-bromo (benzal bromide) compounds with the mono-bromo compounds predominating. The majority of the product is one half-way to the aldehyde oxidation level. Using the DBDMH, the major if not the sole product is the desired di-bromo compound with the oxidation being complete.

The previously mentioned prior U.S. Patent 4,335,263, which discloses the use of the molecular bromine as the bromination agent, also discloses N-bromosuccinimide (NBS) as a brominating agent although no examples are presented using this material. One of the advantages of the DBDMH brominating agent of the present invention over NBS brominating agent is cost. The DBDMH is less expensive by a factor of about four. Another advantage is that the DBDMH contains two bromine atoms whereas NBS contains only one. Therefore, the total weight of DBDMH needed to provide the bromine loading needed is less by a factor of 0.8 as compared to NBS. This is an advantage because of the reduced cost to handle the reduced mass of brominating agent. A third advantage is that the degree of recovery of the organic carrier molecule after the brominating step for recycle to produce fresh brominating agent is much greater and easier using DBDMH. Using NBS, there is a greater disposal problem and environmental impact. A sufficient quantity of the brominating agent is used to transfer two bromine atoms from the reagent to each molecule of the alkylated methylcatechol.

The solvent for the brominating reagent has a boiling point between 65° C. and 90° C., preferably 72° C. to 82° C. Preferred solvents are exemplified by carbon tetrachloride and heptane. Other solvents which could be used include cyclohexane, chloroform, trichloroethane, benzene, ethers (diethyl ether, tetrahydrofuran, methyl t-butylether, etc.), acetone and 2-butanone. Also esters such as ethyl acetate, propyl acetate, iso-butyl acetate, etc., might be used.

The reaction is started by the addition of a radical initiator which, when subjected to a sufficiently high reaction temperature, undergoes a homolytic bond cleavage. Thus one molecule of initiator forms two radical molecules. The radical molecules react with either the starting material or the organic bromine-transfer reagent to make new radicals from these compounds. Once this has been achieved, the radical chain reaction has been initiated and propagation carries the chemical process to completion. The initiators of the present invention are those which are highly reactive and which have a ten hour half-life temperature in the range of 47° to 55° C. Examples are 2,2'-azobis-2,4-dimethylpentanenitrile (VAZO 52 from DuPont), t-butyl peroxyneoheptanoate, t-amyl peroxypivalate, t-butyl peroxyneodecanoate and t-butyl peroxypivalate but other initiators can be used as long as they are highly reactive and have the required ten-hour half-life temperature. This temperature range is an indication of the temperature at which the initiator decomposes to form free radicals at the specified rate. The organic portion of the brominating reagent is recovered by filtration and stored for recycle. The dibromide that is formed is not isolated but is immediately used in the subsequent reaction. Although chlorine-containing reagents are sufficiently reactive to perform the same function as the bromine reagents, the chlorine radical actually possesses reactivity greater than that required for exclusive reaction at methyl groups on an aromatic ring. The result usually observed is that of chlorine incorporation on the aromatic ring, as well as other undesired side reactions. In contrast to chlorine, the radical generated from bromine has a reactivity sufficient to perform chemical reactions only at methyl groups attached to an aromatic ring.

The next step in the process of the present invention is the hydrolysis of the dibromide by treatment with water, a miscible organic solvent and an acid scavenger to form the benzaldehyde product. The miscible organic solvent may be selected from such solvents as tetrahydrofuran, methanol, ethanol, dimethylsulfoxide, acetone and similar solvents. The only requirements for the organic solvent is that it be miscible with water and non-reactive with water, potassium carbonate or the dibromide. The acid scavenger is for the purpose of neutralizing the hydrobromic acid that is liberated by hydrolysis of the dibromide and may, for example, be a tertiary amine or an inorganic carbonate, preferably sodium carbonate. In the instance of dibromides prepared from 3-methylcatechol, it is advantageous to add dimethylsulfoxide to the hydrolysis reaction at a level of about 2.5 molar equivalents or more to accelerate the rate of hydrolysis. Unlike the previously mentioned U.S. Pat. No. 4,335, 263 wherein dimethylsulfoxide is used as an oxidizing agent, the function is quite different in the present invention where all of the oxidation is already completed and the dimethylsulfoxide is simply a nucleophilic reagent facilitating hydrolysis of the dibromide.

The hydrolysis of the dibromide forms the product benzaldehyde which is isolated from the aqueous reaction mixture in a known manner by extraction with an organic solvent and then removal of the organic solvent by simple distillative methods to provide essentially pure benzaldehyde.

The following example describes certain equipment, materials and methodologies for practicing the invention. However, other equipment, materials and methodologies can be employed within the scope of the invention.

EXAMPLE

Step No. 1

3,4-Dimethoxytoluene

In a 12 liter flask was placed 500.0 grams of 4-methylcatechol, 4 liters of methylene chloride, 216.6 grams of a phase transfer catalyst such as described in U.S. Pat. No. 3,992,432 and sold commercially under the trademark Adogen 464, 4 liters of water and 483.0 grams of sodium hydroxide pellets. The mixture was mechanically stirred as 1.144 liters of dimethyl sulfate was added dropwise over 5 hours at ambient temperature. The reaction was stirred for an additional hour and then the phases were separated. The aqueous phase was divided into two equal portions. Each portion was extracted with fresh methylene chloride (2×500 mL). The combined organic layers were dried over anhydrous magnesium sulfate, filtered and concentrated on a rotary evaporator to provide a red, transparent oil having a mass of 1126.4 grams. The material was divided into two equal portions and purified by vacuum fractional distillation. Impure cuts from the distillations were combined and redistilled. A total of 4 pure fractions were obtained, having a total mass of 543.9 grams, 88.7% yield, of 3,4-dimethoxytoluene.

Alternate Step No. 1

3,4-Dimethoxytoluene

In a 1 L, 3-necked flask was placed 500.0 g of 4-methylcatechol (4.03 mole, 1.0 eq.), 808 mL of toluene (5 mole/L) and 404 mL of water (10 mole/L). The flask was fitted with an overhead mechanical stirrer, thermocouple probe and a dropping funnel. The dropping funnel was charged with 357.1 g of sodium hydroxide (8.86 mole, 2.2 eq.) dissolved in 748 mL of water (11.8 mole/L). Dimethyl sulfate (838 mL, 8.87 mole, 1.1 eq.) was added to the flask. The contents of the flask were stirred well and the sodium hydroxide solution was added slowly to the flask. The temperature of the reaction rose to 35° C., at which point the addition of sodium hydroxide was slowed, such that the temperature did not exceed 35° C. External cooling by means of a chilled water bath applied. After the addition of sodium hydroxide was complete, the flask was removed from the chilled water bath and stirred until the temperature of the mixture returned to room temperature (~1.5 hours). Stirring was stopped. The phases were separated. The aqueous phase was extracted with fresh toluene (150 mL). The combined organic phases were dried over anhydrous potassium carbonate, filtered and concentrated by fraction distillation at atmospheric pressure. The crude product was purified by vacuum fractional distillation to provide a total of 559.6 g of the desired product.

Step No. 2

3,4-Dimethoxybenzaldehyde

In a 5 L flask equipped with mechanical stirrer and reflux condenser were placed 100.0 g (0.657 mol) of 3.4-dimethoxytoluene, 2.64 L of cyclohexane (0.25 M), and 104.5 g (0.986 mol) of anhydrous sodium carbonate. The apparatus was flushed with argon. The mixture was stirred and heated to reflux while continuing to sweep argon gently over the solution. A mixture of 197.28 g of 1,3-dibromo-5, 5-dimethylhydantoin (DBDMH, 0.69 mol, 1.05 eq.) and 4.08 g 2,2'-azobis- 2,4-dimethylpentanenitrile (VAZO-52, 0.016 mol, 0.025 eq.) were gradually added through a funnel to the solution over a period of 120 minutes. After addition of the mixture was complete, the reaction mixture was allowed to stir for another thirty minutes at reflux. The solution was allowed to cool to room temperature and the solids was removed by vacuum filtration. The receiver flask contained 122.0 g of sodium carbonate monohydrate. The cyclohexane was removed in vacuo. To the residue was added 600 mL of water and 600 mL of tetrahydrofuran. The solution was mechanically stirred and heated to reflux for two hours. After cooling, the tetrahydrofuran was removed in vacuo. The aqueous solution was extracted three times with 200 mL of methyl tert-butyl ether. The organic extract was dried with anhydrous magnesium sulfate. After removing the magnesium sulfate by vacuum filtration through a fritted funnel, the methyl tert-butyl ether was removed in vacuo to provide 120.6 g of crude veratraldehyde (0.725 mol, 110.4% yield) that was shown to be 74.9% pure by GC and 77.4% pure by HPLC. The product was purified by bulb-to-bulb distillation to provide 72.2 g of veratraldehyde (0.434 mol, 66.1% yield, 94.1% pure by GC, 97.2% pure by HPLC). The distilled material was dissolved in 1.5 volumes (108 mL) of toluene and 1.5 volumes of cyclohexane and allowed to sit overnight in a freezer. The crystals were collected the following morning by vacuum filtration. The filter cake was washed liberally with cyclohexane. After drying in vacuo, 53.7 g (0.323 mol, 49.2% yield, 100.0% pure by HPLC, 99.2% pure by GC) of white crystalline veratraldehyde was collected.

Step No. 3

2-(3,4-dimethoxypheny)-nitroethene

In a 250 mL flask was placed 42.45 g of 3,4-dimethoxybenzaldehyde (0.255 mole, 1 eq.), 64 mL of glacial acetic acid (4.0 M), 9.83 g of ammonium acetate (0.128 mole, 0.5 eq), and 15.2 mL of nitromethane (0.281 mole, 1.1 eq.). The mixture was stirred well and heated to reflux for 1.5 hour and allowed to cool to room temperature. The reaction mass solidified and was dissolved in methylene chloride (500 mL) and washed with water (2×400 mL). The organic layer was dried over anhydrous magnesium sulfate, filtered and concentrated on a rotary evaporator to provide 56.33 g of crude product. Crystallization of the product from ethanol (240 mL) and acetone (100 mL) provided 28.66 g of 2-(3,4-dimethoxypheny)-nitroethene (0.137 mole), 53.7% yield.

Step No. 4

Homoveratrylamine

In a 3 L flask, containing an argon atmosphere, fitted with a dropping funnel and condenser, was placed 800 mL of a 1.0 M solution of borane in tetrahydrofuran. To the stirred solution was added a solution of 33.47 grams of 2-(3,4-dimethoxypheny)-nitroethene in 800 ml of tetrahydrofuran, at such a rate (~3 hours) that the temperature of the solution in the flask did not exceed 35° C. The mixture was heated to reflux for 20 hours and then allowed to cool to room temperature. The excess borane was quenched by careful addition of methanol (97 mL). The mixture was concentrated on a rotary evaporator. The residue was diluted with methanol (670 mL) and 2.0N HCl (670 mL). The mixture was heated to reflux for 1 hour. The methanol was removed on a rotary evaporator. The aqueous solution was extracted with diethyl ether (2×800 mL) to remove the neutral impurities. The pH of the aqueous solution was adjusted to 12—

14 with sodium hydroxide pellets (66.88 g), then extracted with ether (3×800 mL). The organic layers were separately dried over anhydrous sodium sulfate, filtered and concentrated on a rotary evaporator to provide 2.14 grams of neutral by-products and 31.65 grams of crude homoveratrylamine. Purification of the homoveratrylamine by bulb-to-bulb distillation (110° C. @ 0.6 mm Hg) provided 24.78 grams of the desired product, 85.5% yield.

A major advantage of the present invention is that it uses a safe-to-handle organic bromide reagent which is converted to organic compounds insoluble in the reaction solvent. The spent reagent may be collected and recycled to provide the appropriate bromine-containing reagent. Further, it is possible to recycle the bromide that is released from the catechol during the hydrolysis step. Thus, both the reagent molecule and the bromide may be recycled, providing a cost effective method for the oxidation of methyl catechol derivatives to the corresponding benzaldehydes. The resulting environmental impact of the process is low.

Many modifications of the processes described above may be made by those skilled in the art to achieve results to suit specific needs or objectives without departing from the scope of the invention described and claimed herein.

I claim:

1. A method for the conversion of methylcatechol to a corresponding alkoxy benzaldehyde comprising the steps of:

a. converting the hydroxyl groups of said methylcatechol to alkoxy groups by alkylation thereby forming alkylated methylcatechol;

b. adding a non-reactive, non-polar solvent having a boiling point in the range of 65° C. to 90° C. to said alkylated methylcatechol and heating under reflux conditions in said range of 65° C. to 90° C.;

c. gradually adding a mixture of a brominating agent comprising 1,3-dibromo-5,5-dimethylhydantoin and a free radical initiator having a ten hour half-life in the temperature range of 47° C. to 55° C. over a period of time to said refluxing alkylated methylcatechol whereby the benzylic methyl groups of said alkylated methylcatechol are dibrominated to form methyl dibromide groups without significant formation of methyl monobromide groups and without any significant bromination of the aromatic ring of said methyl catechol; and d. hydrolyzing said methyl dibromide groups thereby forming said corresponding alkoxy benzaldehyde.

2. A method as recited in claim 1 wherein said free-radical initiator is selected from the group consisting of 2,2'-azobis-2,4-dimethylpentanenitrile, t-butyl peroxyneoheptanoate, t-amyl peroxypivalate, t-butyl peroxyneodecanoate and t-butyl peroxypivalate.

3. A method as recited in claim 1 wherein said non-reactive, non-polar solvent is selected from the group consisting of carbon tetrachloride, chloroform, cyclohexane, trichloroethane, benzene, ethers, acetone, 2-butanone, esters and heptane.

4. A method as recited in claim 2 wherein said free radical initiator is 2,2'-azobis-2,4-dimethylpentanenitrile.

* * * * *